(12) United States Patent
Sessions et al.

(10) Patent No.: US 6,768,040 B1
(45) Date of Patent: Jul. 27, 2004

(54) WOUND DRESSING FOR TREATING INJURY TO NASAL PASSAGES

(75) Inventors: Robert W. Sessions, Hinsdale, IL (US); Richard A. Rodzen, Bollingbrook, IL (US)

(73) Assignee: Ferris Pharmaceuticals Inc., Burr Ridge, IL (US)

( * ) Notice: Subject to any disclaimer, the term of this patent is extended or adjusted under 35 U.S.C. 154(b) by 0 days.

(21) Appl. No.: 09/536,649

(22) Filed: Mar. 27, 2000

(51) Int. Cl.[7] .............................................. A61F 13/00
(52) U.S. Cl. ............................ 602/56; 602/41; 602/46; 128/206.11
(58) Field of Search ........................... 128/206.11, 858; 602/41–42, 46, 56, 74; 604/11, 301, 304, 307

(56) References Cited

U.S. PATENT DOCUMENTS

| | | | |
|---|---|---|---|
| 3,499,448 A | * | 3/1970 | Jones |
| 3,559,646 A | * | 2/1971 | Mullan |
| 3,794,024 A | * | 2/1974 | Kokx et al. |
| 4,098,728 A | * | 7/1978 | Rosenblatt .................. 521/141 |
| 4,217,900 A | * | 8/1980 | Wiegner et al. |
| 4,605,401 A | * | 8/1986 | Chmelir |
| 5,064,653 A | | 11/1991 | Sessions et al. |
| 5,065,752 A | | 11/1991 | Sessions et al. |
| 5,112,348 A | * | 5/1992 | Glassman |
| 5,201,326 A | * | 4/1993 | Kubicki et al. |
| 5,254,301 A | | 10/1993 | Sessions et al. |
| 5,336,163 A | * | 8/1994 | DeMane et al. ............... 602/46 |
| 5,387,206 A | * | 2/1995 | Valentine et al. ........... 604/358 |
| 5,916,928 A | | 6/1999 | Sessions et al. |
| 5,954,682 A | * | 9/1999 | Petrus ........................... 604/1 |

OTHER PUBLICATIONS

XOMED Rhinology Products.*
Medtronic Xomed Surgical Products; copy of Rhinology Head and Neck Products brochure of nasal splint and packing systems; applicants first became aware of this material no later than Mar. 26, 2000.
Medtronic Xomed Surgical Products; copies of Rhinology Products: Nasal and Sinus Packing catolog pages of various packing nasal packing products; applicants first became aware of this material no later than Mar. 26, 2000.

* cited by examiner

*Primary Examiner*—Nicholas D. Lucchesi
*Assistant Examiner*—Lalita M. Hamilton
(74) *Attorney, Agent, or Firm*—Leydig Voit & Mayer, Ltd.

(57) ABSTRACT

Wound dressing for a nasal cavity comprising a flexible, porous polyurethane-based foam comprising a liquid-absorbing component, wherein the dressing is provided in a in a shape acceptable for insertion into a nasal cavity, e.g., cylindrical, conical or frustro-conical shape.

16 Claims, 2 Drawing Sheets

WOUND DRESSING FOR TREATING INJURY TO NASAL PASSAGES

TECHNICAL FIELD OF THE INVENTION

This invention pertains to wound dressings, and more particularly to dressings for treating trauma to the nasal passages.

BACKGROUND OF THE INVENTION

A number of different dressings have been used over the years to assist in treating damage to the nasal passages due to surgical procedures or injury. While many of these dressings reduce bleeding, they suffer from various deficiencies.

For example, in the case of polyvinylacetate (PVA) dressings, as the wound heals, and the liquid absorbed by the dressing evaporates, the dressing can become dry. As it dries, the dressing becomes adhered to the nasal cavity. Removal of the dressing in such cases also removes the newly formed tissue from the wound bed, causing pain and reinjury to the nasal cavity.

Moreover, PVA dressings are also uncomfortable to patients, being relatively inflexible and brittle upon insertion. Further, such dressings can experience a size increase in excess of about 20 times upon absorption of wound exudate, causing certain difficulties in removal.

A need thus exists for a wound dressing that addresses the foregoing and other problems in the treatment of damages to the nasal passages.

BRIEF SUMMARY OF THE INVENTION

The present invention addresses the foregoing and other needs by providing a wound dressing comprising a flexible, porous polyurethane-based foam comprising a liquid-absorbing component, wherein the foam is provided in a cylindrical, conical or frustro-conical shape.

The inventive dressing comprises a polyurethane foam which provides a relatively high degree resistance to wound adhesion. This resistance is believed to be provided at least in part by the inclusion of a liquid absorbing component in the foam, which assists in retaining moisture within the dressing. The dressing remains sufficiently moist during treatment, permitting subsequent removal of the dressing without inflicting significant new injury to the nasal passage.

The dressing further possesses only a minor degree of swelling, which also helps in minimizing discomfort, and easing removal. The flexibility of the dressing further assists in both insertion and removal.

The dressing of the present invention is further surprising because it provides good results in nasal therapy regardless of the average pore size of the dressing. Prior to the discovery of the present invention, a belief existed in the art that dressings with relatively small average pore sizes would preclude excessive tissue growth into the dressing, and thereby minimize damage to the wound bed upon removal. The present invention runs contrary to this belief.

The invention may best be understood with reference to the accompanying drawings and in the following detailed description of the preferred embodiments.

The present invention is described in the following paragraphs with an emphasis on preferred embodiments. However, it will be obvious to those of ordinary skill in the art that variations of the preferred embodiments may be successfully used, and that it is intended that the invention may be practiced otherwise than as specifically described herein. The inventive dressings should therefore not be construed as being limited to the preferred embodiments described herein.

DETAILED DESCRIPTION OF THE INVENTION

The present invention provides a wound dressing for insertion into the nasal passage of an animal, preferably a human. The dressing comprises a flexible, porous, low-swelling polyurethane-based foam comprising a liquid-absorbing component, wherein the foam is provided in a shape suitable for insertion into the nasal cavity, advantageously substantially cylindrical, conical or frustro-conical in shape.

Figure 1:
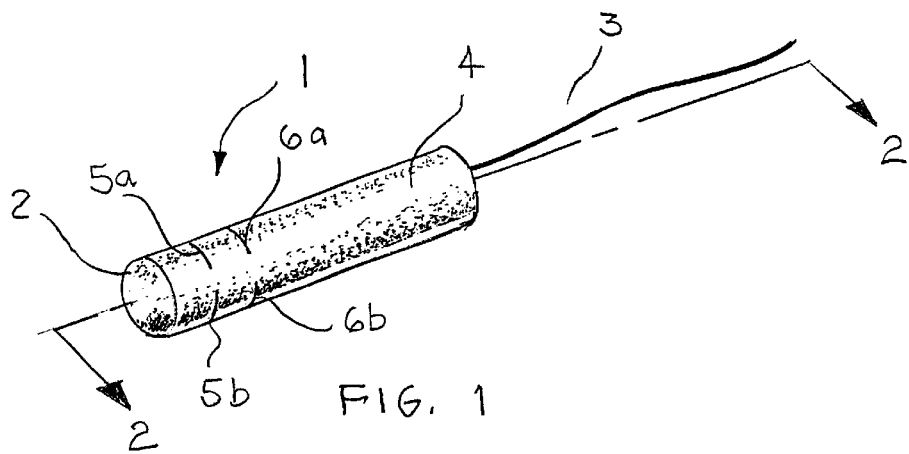
FIG. 1 is a perspective view of one preferred embodiment of the wound dressing of the present invention, wherein the dressing is cylindrical in shape.

Turning initially to FIG. 1, there is depicted one embodiment of the inventive dressing. In this embodiment, the flexible, porous polyurethane-based foam dressing 1 is shown in a cylindrical shape. One end of the dressing 2 advantageously may be rounded, e.g., semi-spherical, to assist in insertion of the dressing into the nasal passage. The other end of the dressing 1 may optionally include a tether 3. The tether 3 assists in removal of the dressing when necessary. The tether 3 may comprise any medically suitable material of sufficient strength to avoid breakage upon removal of the dressing, and may be attached by any suitable means. Like the polyurethane foam 4, the tether is preferably sterilizable. Most preferable, the tether is a material comprising cotton or nylon which becomes bound within the polyurethane foam 4 after curing, thereby anchoring the tether thereto.

Figure 3:
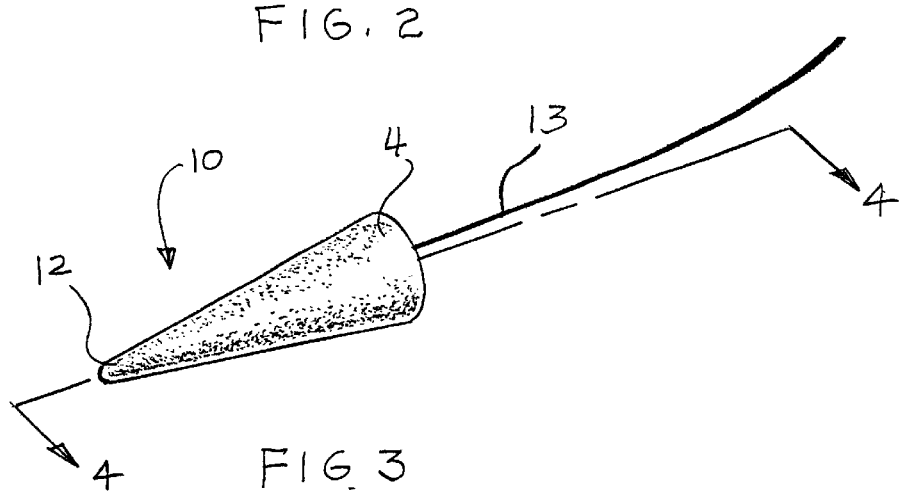
FIG. 3 is a perspective view of a second preferred embodiment of the wound dressing of the present invention, wherein the dressing is conical in shape.
Figure 4:
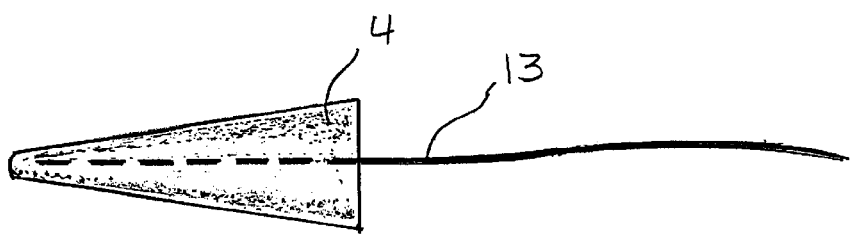
FIG. 4 is a side view of the preferred wound dressing shown in FIG. 3.
Figure 5:
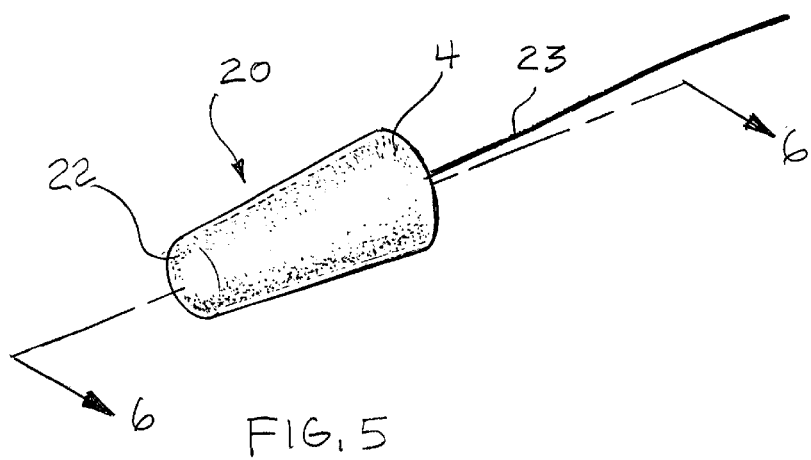
FIG. 5 is a perspective view of a second preferred embodiment of the wound dressing of the present invention, wherein the dressing is frustro-conical in shape.
Figure 6:
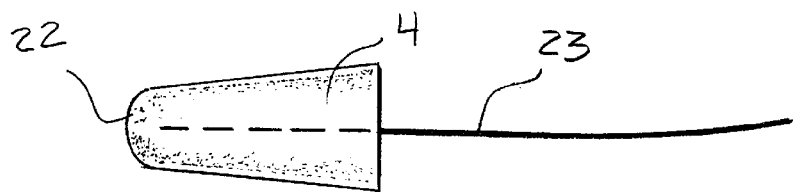
FIG. 6 is a side view of the preferred wound dressing shown in FIG. 5

FIGS. 3 and 5 depict alternative embodiments of the inventive dressings. The former shows the dressing in a conical shape 10, while the latter shows the dressing in a frustro-conical shape 20. As in the case of the embodiment of FIG. 1., one end of these dressings may be rounded to assist in insertion 12, 22, while the other end may include a tether 13, 23.

A further, yet optional, enhancement to the inventive dressings is shown in FIG. 1, but may be applied to the other embodiments described herein as well. This option contemplates the inclusion of a plurality of perpendicular slits in the foam material, e.g., 5a, 5b, 6a, 6b, these slits extending generally inward from the outer surface of the dressings. These slits are preferably provided in sets, e.g., 5a, 5b and 6a, 6b, with each set located along the longitudinal axis of the dressing. When included, the slits provide any easy means of sizing the dressings to provide for a custom fit of the dressing to a particular nasal passage. Preferably, the slits are sufficiently deep to permit removal of the undesired dressing portion by hand. If such slits are used, the tether, which could impede hand removal of the undesired material, should not underlie such slits.

Figure 7:
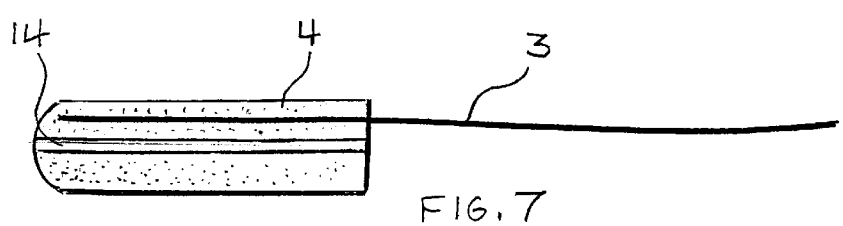
FIG. 7 is a cross-sectional side view of an alternative embodiment of the preferred wound dressing of the present invention, wherein the dressing is cylindrical in shape.
Figure 1:
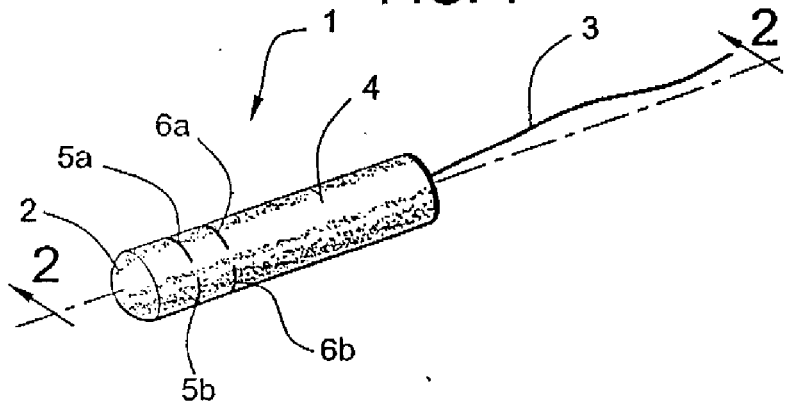
Figure 2:
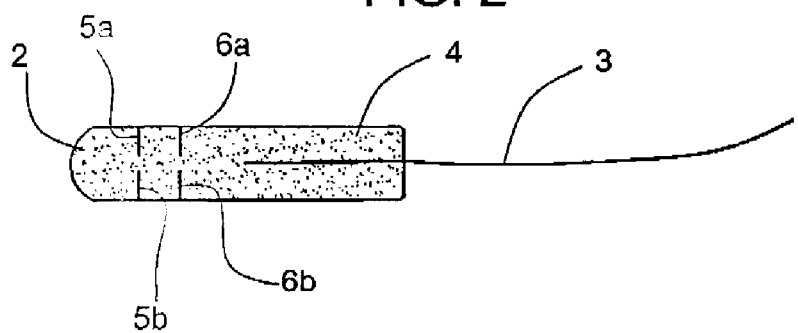
Figure 3:
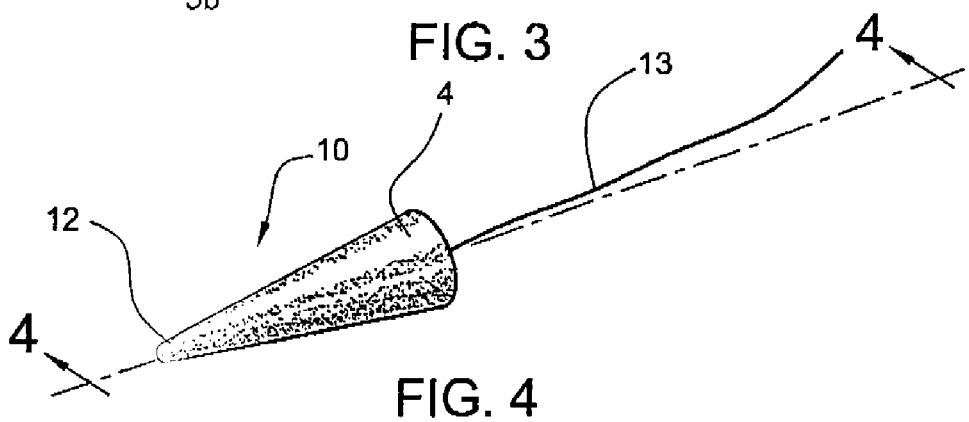
Figure 4:
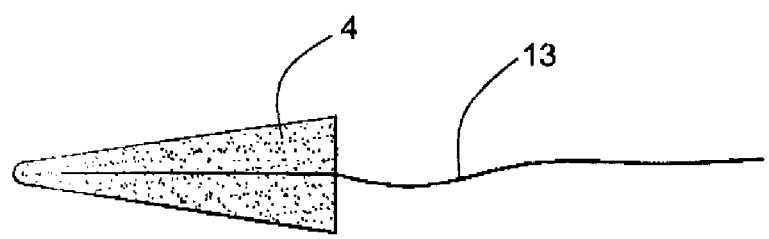
Figure 5:
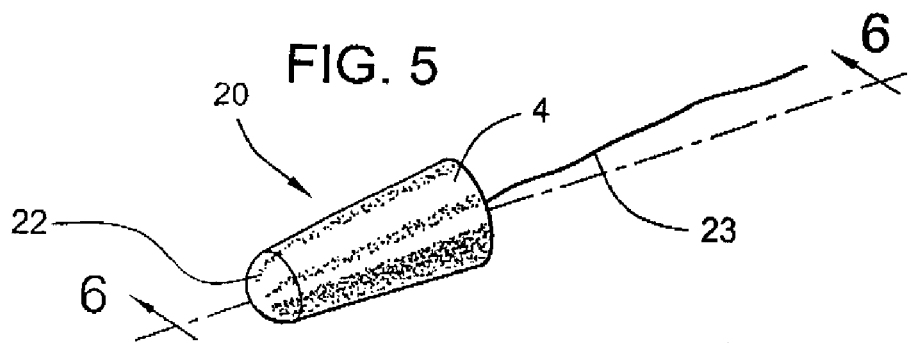
Figure 6:
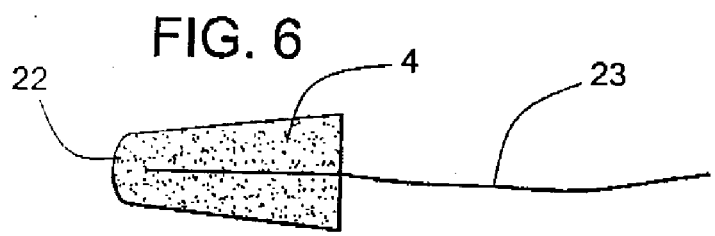
Figure 7:
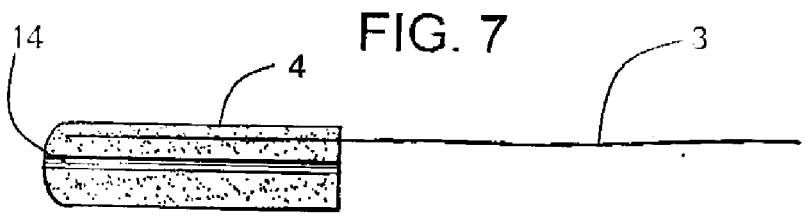
Figure 8:
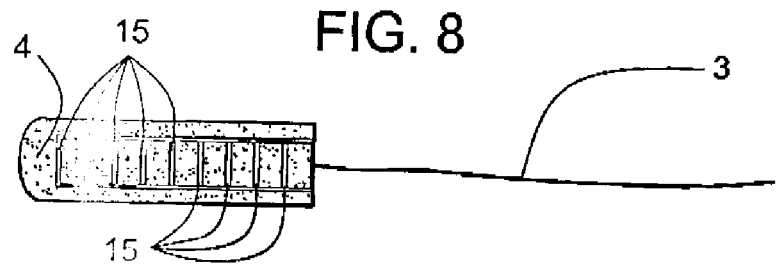
Figure 9:
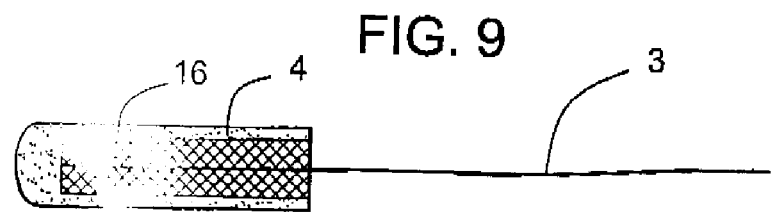

A further optional enhancement is a breathing passage 14, as illustrated in FIG. 7. It should be understood, however, that such a passage may be applied to any of the embodiments described herein. If desired, the breathing passage may be provided by molding the dressing around a flexible, yet crush-proof tube, or by molding (or alternatively cutting) a passage into the dressing during manufacturing.

Figure 2:
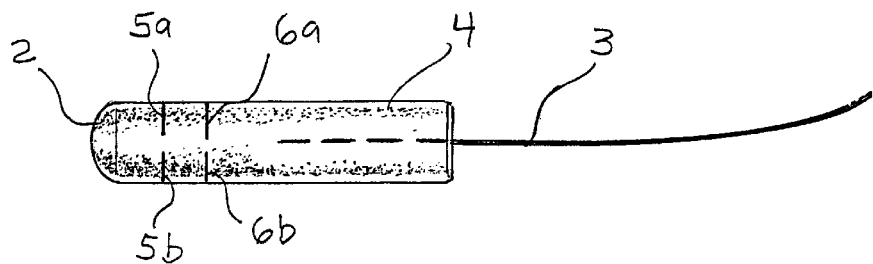
FIG. 2 is a side view of the preferred wound dressing shown in FIG. 1.
Figure 8:
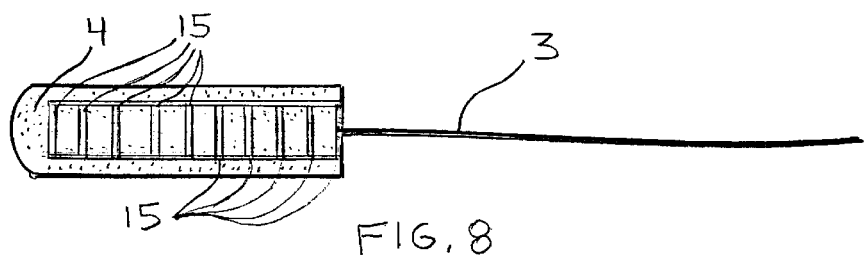
FIG. 8 is a cross-sectional side view of another alternative embodiment of the preferred wound dressing of the present invention, wherein the dressing is cylindrical in shape.
Figure 9:
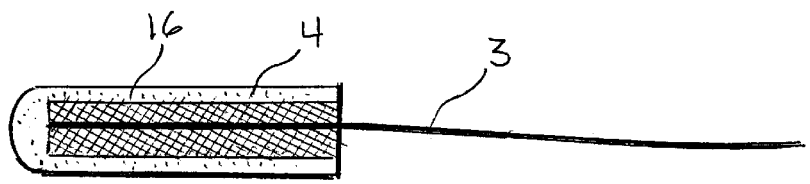
FIG. 9 is a cross-sectional side view of yet another alternative embodiment of the preferred wound dressing of the present invention, wherein the dressing is cylindrical in shape.

The present invention contemplates that the polyurethane foam will directly contact the injured portion of the nasal passage. In this regard, the foam may surround a support material, e.g., a flexible plastic frame 15, creating a hollow tube-like structure, or may surround a mesh 16, as shown in FIGS. 8 and 9, respectively. In a preferred embodiment, however, and as depicted in FIGS. 1 and 2, the dressing is substantially solid polyurethane foam 2, with the tether 3 extending well into, and preferably substantially through, the length of the dressing. The latter assists in ensuring the tether is well anchored to the polyurethane foam.

The dressing may be prepared from any type of polyurethane foam that is flexible and porous. Advantageously, the foam is free of medical-grade silicone additives. More specifically, a flexible foam is one that can be folded over upon itself without exhibiting cracking or breaking. A porous foam is one that includes open pores on its exterior surface, enabling liquids to penetrate the interior of the foam. The foam further swells only minimally in the presence of liquids, less than about 3 times its original nominal diameter, and preferably less than about 2 times its nominal diameter. Most preferably, the foam is the polyurethane foam described in U.S. Pat. Nos. 5,064,653, 5,065,752, 5,254,301 and 5,916,928.

The liquid-absorbing component, as discussed herein, can include almost any type of liquid absorbing particles, but preferably correspond to the absorbent powders described in the foregoing patents. As mentioned previously, the anti-adhesive properties of the inventive dressings are believed to be primarily provided by the inclusion of the absorbent powers, due to the moisture retention properties of the latter. However, it is also believed that the anti-adhesive properties may be further positively affected by including effective amounts of wetting agents and adjuvants.

Any suitable method may be used to provide the dressing in the foregoing shapes, e.g., die cutting of the foam into the desired shape, casting, or injection molding. While die cutting is the easiest method, it is also labor intensive. For this reason, molding is contemplated as the preferred method of providing the dressing.

It should be appreciated that minor variances in the dressing shapes described herein that do not detract from the advantages of the present invention are intended to be included within the scope of the present invention.

All of the references cited herein, including patents, patent applications, and publications, are hereby incorporated in their entireties by reference. Further, any reference herein to a component in the singular is intended to indicate and include at least one of that particular component, i.e., one or more.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A wound dressing comprising a flexible, uniformly porous polyurethane-based foam comprising a liquid-absorbing component, wherein the dressing is provided in a substantially cylindrical, conical or frustro-conical shape, and the liquid-absorbing component comprises a polymer selected from the group consisting of starch grafted copolymers of acrylate salts, starch grafted copolymers of acrylamide salts, poly-2-propenoic acid, and combinations thereof.

2. The wound dressing according to claim 1, further comprising a tether extending from one end of the dressing to assist in removal of the dressing from a body cavity.

3. The wound dressing according to claim 2, wherein one end of the dressing comprises a semi-spherical shape.

4. The wound dressing according to claim 1, the dressing further comprising perpendicular slits along its length to provide for hand sizing of the dressing.

5. The wound dressing according to claim 1, wherein the dressing is provided in a cylindrical shape.

6. The wound dressing according to claim 1, wherein the dressing is provided in a conical shape.

7. The wound dressing according to claim 1, wherein the dressing is provided in a frustro-conical shape.

8. The wound dressing according to claim 1, the foam further comprising a breathing passage therethrough.

9. The wound dressing according to claim 1, wherein the dressing is low-swelling in the presence of a liquid.

10. The wound dressing according to claim 1, wherein the foam further comprises an adjuvant.

11. The wound dressing of claim 10, wherein the adjuvant is glycerin.

12. A wound dressing comprising a flexible, low-swelling, uniformly porous polyurethane-based foam comprising a liquid-absorbing component, wherein the dressing is provided in a shape acceptable for insertion into a nasal cavity, and the liquid-absorbing component comprises a polymer selected from the group consisting of starch grafted copolymers of acrylate salts starch grafted copolymers of acrylamide salts, poly-2-propenoic acid, and combinations thereof.

13. The wound dressing according to claim 12, further comprising a tether extending from one end of the dressing to assist in removal of the dressing from a body cavity.

14. The wound dressing according to claim 12, the dressing further comprising perpendicular slits along its length to provide for hand sizing of the dressing.

15. The wound dressing according to claim 12, wherein the foam further comprises an adjuvant.

16. The wound dressing of claim 15, wherein the adjuvant is glycerin.

* * * * *

UNITED STATES PATENT AND TRADEMARK OFFICE
CERTIFICATE OF CORRECTION

PATENT NO. : 6,768,040 B1
DATED : July 27, 2004
INVENTOR(S) : Sessions et al.

It is certified that error appears in the above-identified patent and that said Letters Patent is hereby corrected as shown below:

Drawings,
The sheets of informal drawings consisting of Figures 1-9 should be deleted to appear as per attached formal drawings Figures 1-9.

Signed and Sealed this

Fourteenth Day of December, 2004

JON W. DUDAS
*Director of the United States Patent and Trademark Office*